(12) United States Patent
Chiriac et al.

(10) Patent No.: US 10,481,052 B2
(45) Date of Patent: Nov. 19, 2019

(54) QUALITY CONTROL PROCESS TO ASSESS THE ALUMINIZED COATING CHARACTERISTICS OF HOT STAMPED PARTS

(71) Applicant: Ford Global Technologies, LLC, Dearborn, MI (US)

(72) Inventors: Constantin Chiriac, Windsor (CA); Raj Sohmshetty, Canton, MI (US); Elizabeth Bullard, Royal Oak, MI (US); James Engle, Chesterfield, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 105 days.

(21) Appl. No.: 15/937,917

(22) Filed: Mar. 28, 2018

(65) Prior Publication Data

US 2019/0301983 A1    Oct. 3, 2019

(51) Int. Cl.
*G01N 21/00* (2006.01)
*G01N 1/28* (2006.01)
*B21D 22/02* (2006.01)
*B21D 22/20* (2006.01)
(Continued)

(52) U.S. Cl.
CPC .......... *G01N 1/2813* (2013.01); *B21D 22/022* (2013.01); *B21D 22/201* (2013.01);
(Continued)

(58) Field of Classification Search
CPC .......... G01N 1/2813; G01N 3/28; G01N 3/40; G01N 1/36; G01N 2203/0076;
(Continued)

(56) References Cited

U.S. PATENT DOCUMENTS 6,784,989 B2  8/2004  Chapon
8,021,497 B2  9/2011  Fleischanderl et al.
(Continued)

FOREIGN PATENT DOCUMENTS

WO    2014/124749    8/2014

OTHER PUBLICATIONS

Weiss, Z., Quantitative evaluation of depth profiles analysed by glow discharge optical emission spectroscopy: analysi of diffusion proceses, Spectrochimica Acta Part B: Atomic Spectroscopy, Jul. 1992, vol. 47(7), pp. 859-876, Elsevier B.V.
(Continued)

*Primary Examiner* — Abdullahi Nur
(74) *Attorney, Agent, or Firm* — Burris Law, PLLC (57) ABSTRACT

A method of inspecting and determining characteristics of an aluminized coating of a hot stamped part is provided. The method includes removing a sample from the hot stamped part for Glow Discharge Optical Emission Spectrometry (GDOES), analyzing the sample using GDOES, and plotting constituent element weight percentages versus depth on a graph. The method further includes determining points on the graph where constituent elements intersect and where the points of intersection indicate the characteristics of the aluminized coating. The characteristics of the method include, by way of example, a total thickness of the aluminized coating, a thickness of an inter-diffusion layer (IDL), constituents of the aluminized coating, constituents of the hot stamped part, phase composition of the aluminized coating, surface oxidation, and weldability.

20 Claims, 8 Drawing Sheets

(51) Int. Cl.
*G01N 1/36* (2006.01)
*G01N 3/40* (2006.01)
*G01N 3/28* (2006.01)
*G01J 3/443* (2006.01)
*G01N 13/00* (2006.01)

(52) U.S. Cl.
CPC .............. *G01J 3/443* (2013.01); *G01N 1/36* (2013.01); *G01N 3/28* (2013.01); *G01N 3/40* (2013.01); *G01N 2013/003* (2013.01); *G01N 2203/0076* (2013.01); *G01N 2223/61* (2013.01); *G01N 2223/633* (2013.01); *G01N 2291/0234* (2013.01); *G01N 2291/02854* (2013.01); *G01N 2560/00* (2013.01)

(58) Field of Classification Search
CPC ... G01N 2291/02854; G01N 2223/633; G01N 2013/003; G01N 2560/00; G01N 2291/0234; G01N 2223/61; B21D 22/201; B21D 22/022; G01J 3/443
See application file for complete search history.

(56) References Cited

U.S. PATENT DOCUMENTS

| | | |
|---|---|---|
| 8,658,275 B2 | 2/2014 | Toshin et al. |
| 9,200,355 B2 | 12/2015 | Scott et al. |
| 2008/0038143 A1 | 2/2008 | Witt et al. |
| 2009/0103074 A1* | 4/2009 | Cuomo ............... G01J 3/443 356/51 |
| 2014/0342181 A1 | 11/2014 | Mutschler et al. |

OTHER PUBLICATIONS

AZoM, Glow Discharge Optical Emission Spectroscopy (GD-OES)-A Depth Profiling Technique, Apr. 2004, available at URL: https://www.azom.com/article.aspx?ArticleID=2449.

Yang, H.-L. et al., Effect of al content on the microstructure of hot-depped zinc coating on hot stamping steel, Journal of Materials Processing Technology, Jan. 2014, available at URL: https://www.researchgate.net/publication/286129235_Effect_of_al_content_on_the_microstructure_of_hot-depped_zinc_coating-on-hot-stamping-steel.

Bengston, Arne et al., Development of a standard method for quantitative depth profile analysis of zinc-based metallic coatings by direct current glow discharge optical emission spectroscopy, Aug. 1999, available at URL: http://onlinelibrary.wiley.com/doi/10.1002/(SICI)1096-9918(199908)27:8%3C743::AID-SIA568%3/E3.0.CO;2-O/full.

* cited by examiner

QUALITY CONTROL PROCESS TO ASSESS THE ALUMINIZED COATING CHARACTERISTICS OF HOT STAMPED PARTS

FIELD

The present disclosure relates to inspection methods to assess the characteristics of aluminized coatings in hot stamped parts, and more particularly to inspection methods to determine amounts of various constituent elements and layer thicknesses within the aluminized coatings.

BACKGROUND

The statements in this section merely provide background information related to the present disclosure and may not constitute prior art.

The automotive industry typically applies an aluminized coating to the surface of hot stamped boron steel for the purpose of improved oxidation resistance. More specifically, the aluminized coating reduces oxidation of the boron steel during austenitization at temperatures of 880 to 930° C. Unfortunately, the aluminized coating limits many hot stamping process parameters including, but not limited to furnace dew point, furnace residence time, furnace temperature, and furnace dwell time.

As the aluminized boron steel is austenitized, the aluminized coating thickness increases as the Aluminum diffuses into the steel. Similarly, the Iron diffuses into the aluminized coating. The coating layer at the interface between the steel and aluminized coating represents the inter-diffusion layer (IDL). The resultant thicknesses for the aluminized coating and the IDL depend on process parameters including but not limited to the furnace dew point, furnace temperatures, and furnace dwell or residence times. The resultant thicknesses correlate to the weldability and paintability of the hot stamped part.

Current industrial Quality Control (QC) practice has been to assess and inspect development and growth of the aluminized coating, following the hot stamping process, by measuring the IDL thickness at the steel-coating interface by using optical microscopy (i.e. optical light microscopy or OLM). OLM is also used to measure the total thickness of the aluminized coating. These QC methods include sampling the hot stamped part followed at least by the sample preparation steps of:

Mounting the samples with an adhesive to create metallographic samples;
Grinding the metallographic samples;
Polishing the metallographic samples; and
Etching the metallographic samples;

Following sample preparation, optical microscopic analysis is performed on the etched metallographic samples so that measurements of the thickness of interest are determined. Some of the limitations of these QC methods include:

Long lab processing times, about four (about 4) hours from sampling to OLM analysis, to obtain the coating thickness measurement results;
Significant material is wasted or scrapped to obtain acceptable surface quality for OLM measurements;
The thickness measurements are highly dependent on the verticality of the adhesive mounting as slight inclinations from vertical result in large increases in thickness measurements (parts out of tolerance) potentially resulting in unnecessary scrapping or rework;
The IDL thickness measurements are dependent on the quality of chemical etch, the calibration accuracy of the optical microscope, operator experience, the location on the sample, and various other factors;
The total coating thickness measurements are dependent on the quality of the metallographic sample preparation, particularly near sample edges where minor preparation mistakes lead to large inaccuracies in the measurements; and
The QC OLM measurements are taken very locally (approximately 0.3 mm) at high magnification (500×) and often do not represent the entire surface of the hot stamped part.

The present disclosure addresses the issue of time-consuming QC procedures in measuring the various thicknesses and constituents of aluminized coatings on the surface of hot stamped boron steels, among other issues related to measuring and characterizing coatings on various substrate materials.

SUMMARY

In one form of the present disclosure, a method of inspecting and determining characteristics of an aluminized coating of a hot stamped part is provided. The method comprises removing a sample from the hot stamped part for Glow Discharge Optical Emission Spectrometry (GDOES), analyzing the sample using GDOES and plotting constituent element weight percentages versus depth on a graph and determining points on the graph where constituent elements intersect. In this method of the present disclosure, the points of intersection indicate the characteristics of the aluminized coating. The characteristics may include by way of example, a total thickness of the aluminized coating, a thickness of an inter-diffusion layer (IDL), constituents of the aluminized coating, phase composition of the aluminized coating, surface oxidation, and weldability, among others.

When the hot stamped part is coated with a eutectic $AlSi_{10}Fe_3$ alloy, an intersection between Aluminum and Carbon indicates the total thickness of the aluminized coating. Further, a difference between an intersection of Aluminum and Carbon and a second maximum Silicon weight percent (wt. %) indicates the thickness of the IDL.

In one form, the analyzed sample size is approximately 5 mm in diameter and the sample does not undergo any preparation prior to being analyzed by GDOES. In another form, the sample may undergo preparation that includes mounting, grinding, and polishing.

In another form, the presence of contamination may be determined by a comparison of constituent elements to a composition of the hot stamped part.

In still another form, the characteristics may be provided to a subsequent manufacturing operation. More specifically, in one form, the characteristics are provided to a controller of an annealing furnace, wherein the controller adjusts a temperature and processing time of the hot stamped part in the annealing furnace based on at least one characteristic. In another form, the total thickness of the aluminized coating and the thickness of the IDL are provided to a subsequent welding operation, wherein welding parameters are adjusted based on at least one of the total thickness of the aluminized coating and the thickness of the IDL.

In another form of the present disclosure, a method of inspecting and determining a total thickness of an aluminized coating and a thickness of an IDL of a hot stamped boron steel part is provided. The method comprises preparing a sample from the hot stamped part for GDOES, analyzing the sample using GDOES and plotting constituent element weight percentages versus depth on a graph and determining points on the graph where constituent elements intersect. In this method of the present disclosure, an intersection between Aluminum and Carbon indicates the total thickness of the aluminized coating, and a difference between an intersection of Aluminum and Carbon and a second maximum Silicon wt. % indicates the thickness of the IDL.

In another form of the present disclosure, a method of controlling a manufacturing operation for hot stamped parts is provided. The method comprises removing a sample from a hot stamped part for GDOES, analyzing the sample using GDOES and plotting constituent element weight percentages versus depth on a graph, and determining points on the graph where constituent elements intersect. In this method of the present disclosure, the points indicate the characteristics of the aluminized coating and the characteristics are provided to a controller of the manufacturing operation, wherein the controller adjusts parameters of the manufacturing operation based on at least one characteristic. The manufacturing operation may include, by way of example, an annealing operation, a shot-blasting operation, or a welding operation, among others.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Generally, the present disclosure provides innovative Quality Control (QC) methods that apply Glow Discharge Optical Spectrometry (GDOES) in a new way to determine the thicknesses of the total coating and the inter-diffusion layer (IDL), among other characteristics of coatings such as aluminized coatings of boron steel.

Figure 1A:
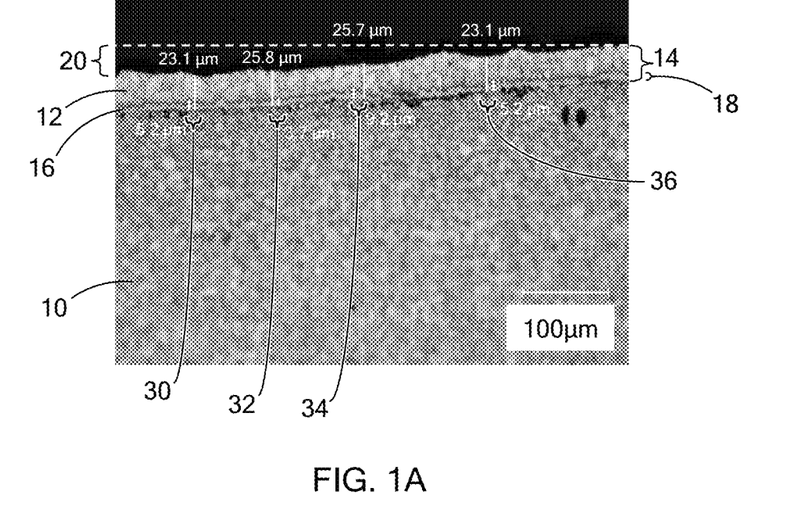
FIGS. 1A through 1D illustrate exemplary optical light microscopy (OLM) micrographs for analyzing an exemplary sample of aluminized 22MnB5 steel following austenitization, according to the investigations of the present disclosure.
Figure 1B:
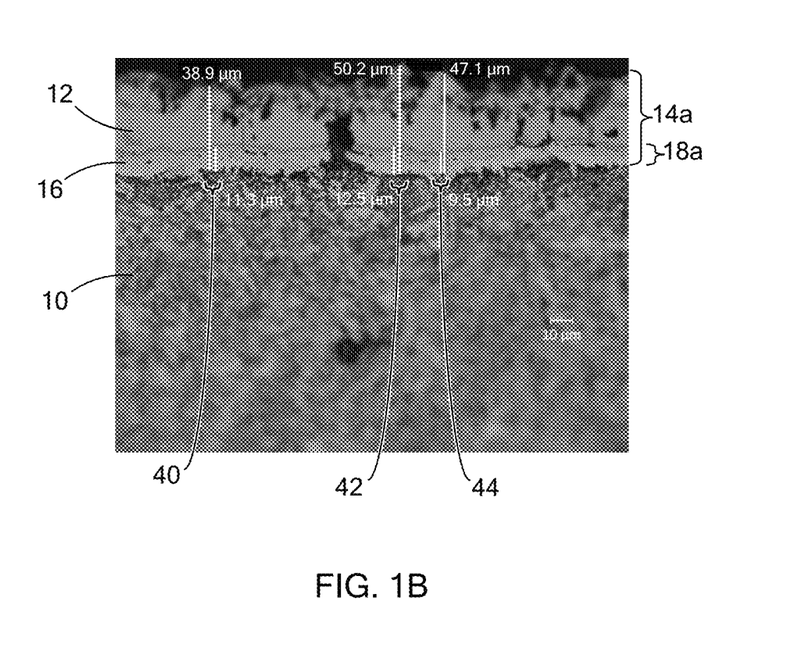
Figure 1C:
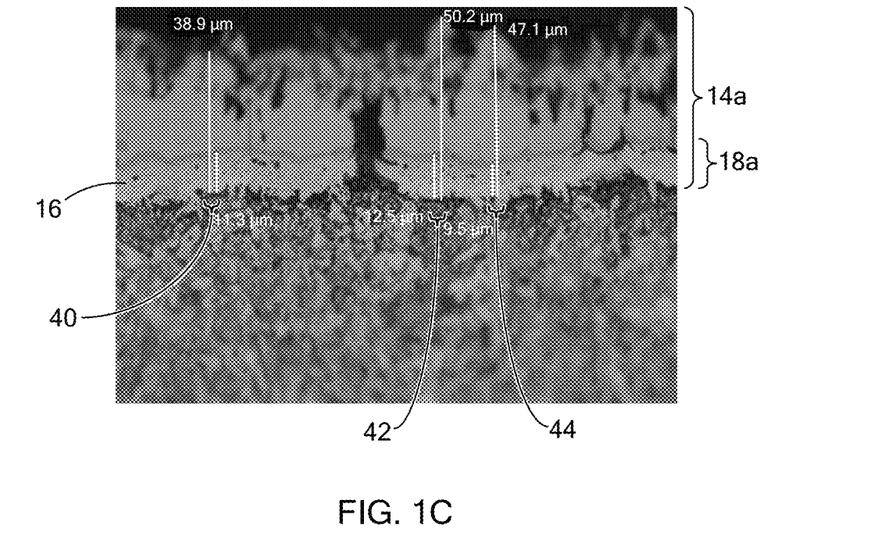
Figure 1D:
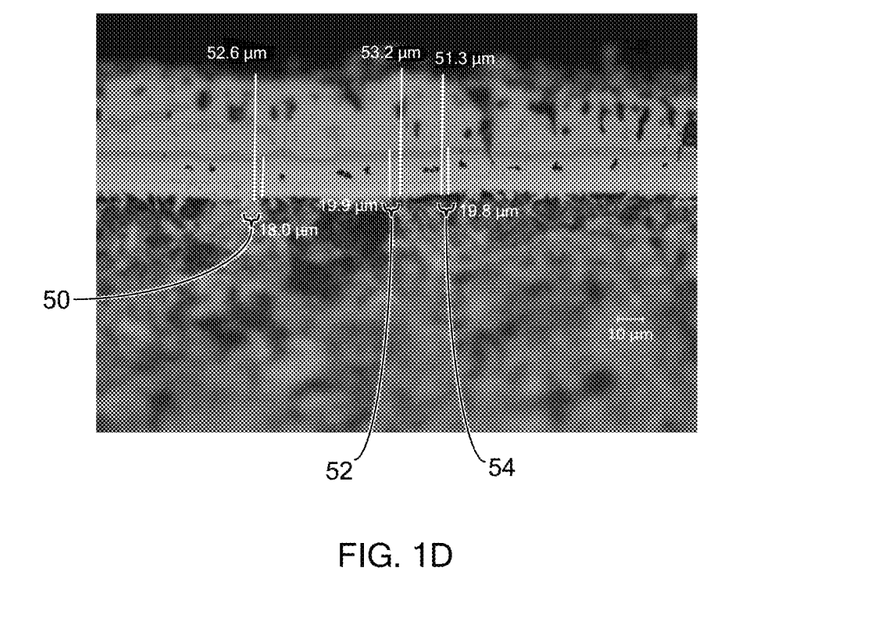

Referring to FIGS. 1A-1D, exemplary optical light microscopy (OLM) analyses of a sample of boron steel 10 with an aluminized coating 12 and an inter-diffusion layer 16 are shown. The aluminized coating 12 has an initial coating thickness 14, the IDL 16 has an initial thickness 18, and the surface of the aluminized coating 12 has an initial average surface roughness 20. As the aluminized boron (22MnB5) steel is austenitized, the aluminized coating thickness increases from 14 to 14a, and the IDL thickness increases from 18 to 18a, as shown in FIG. 1B and FIG. 1C. (FIG. 1C is a cropped and enlarged view of FIG. 1B). The increase in IDL thickness and coating thickness is shown in TABLE 1 below and FIGS. 1A through 1D, with an increase in IDL thickness of about 14.4 µm and an increase in coating thickness of about 29.6 µm. The average surface roughness 20 of the aluminized coating 12 also increases as the austenization progresses.

TABLE 1

| Reference No. | IDL (µm) | Coating (µm) |
|---|---|---|
| FIG. 1A Thicknesses | | |
| 30 | 5.2 | 23.1 |
| 32 | 3.7 | 25.8 |
| 34 | 5.2 | 25.7 |
| 36 | 5.2 | 23.1 |
| Average | 4.83 | 24.43 |
| Standard Deviation | 0.65 | 1.33 |

| Ref. No. | IDL (µm) | Coating (µm) |
|---|---|---|
| FIG. 1B/1C Thicknesses | | |
| 40 | 11.3 | 38.9 |
| 42 | 12.5 | 50.2 |
| 44 | 9.5 | 47.1 |
| Average | 11.1 | 45.4 |
| Standard Deviation | 1.23 | 4.77 |
| FIG. 1D Thicknesses | | |
| 50 | 18 | 52.6 |
| 52 | 19.9 | 58.2 |
| 54 | 19.8 | 51.3 |
| Average | 19.23 | 54.03 |
| Standard Deviation | 0.87 | 2.99 |

The compositions of the aluminized coating and the steel are shown in TABLE 2.

TABLE 2

| Element | Min. wt. % | Max. wt. % |
|---|---|---|
| Aluminized coating | | |
| Iron (Fe) | 0 | ≤3 |
| Silicon (Si) | >0 | ≤10 |
| Aluminum (Al) | Balance | |
| Boron (22MnB5) Steel | | |
| Aluminum (Al) | 0.02 | 0.06 |
| Boron (B) | 0 | 0.005 |
| Carbon (C) | 0.2 | 0.25 |
| Chromium (Cr) | 0 | 0.35 |
| Copper (Cu) | 0 | 0.2 |
| Manganese (Mn) | 1.1 | 1.4 |
| Molybdenum (Mo) | 0 | 0.35 |
| Nitrogen (N) | 0 | 0.009 |
| Phosphorus (P) | 0 | 0.025 |
| Silicon (Si) | 0 | 0.5 |
| Sulfur (S) | 0 | 0.008 |
| Titanium (Ti) | 0.02 | 0.05 |
| Iron (Fe) | Balance plus impurities | |

Figure 2A:
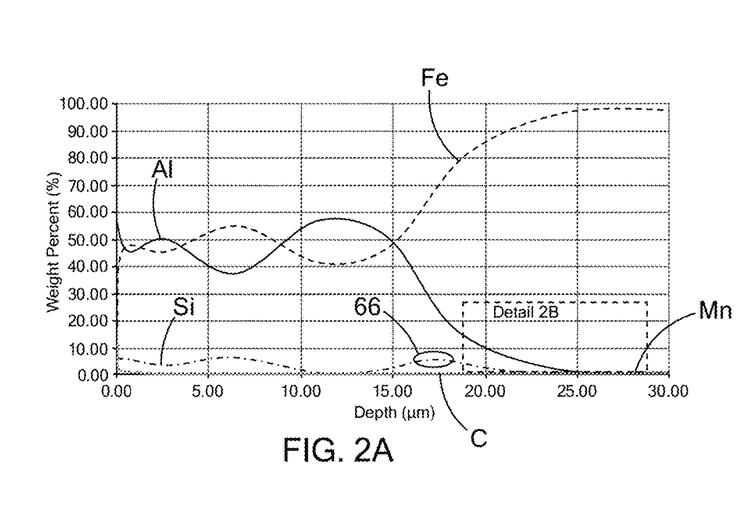
FIG. 2A is a graph showing an exemplary Glow Discharge Optical Emission Spectrometry (GDOES) elemental analysis of a sample of 22MnB5 steel, according to the teachings of the present disclosure.
Figure 2B:
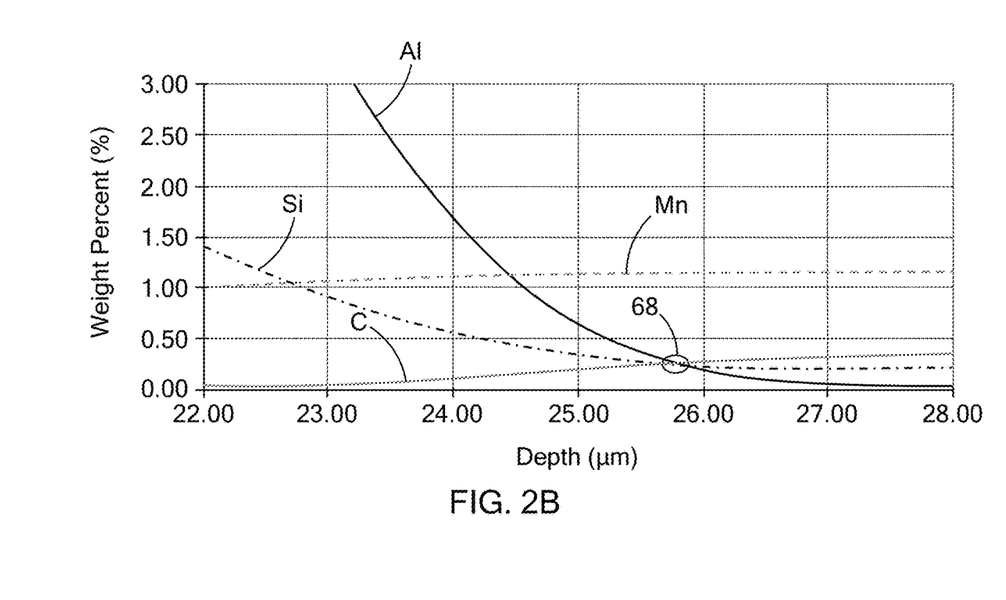
FIG. 2B is a magnified portion of the graph of FIG. 2A.

Now referring to FIGS. 2A and 2B, an exemplary GDOES of a sample of 22MnB5 steel is shown. The weight percent (wt. %) of the elements in TABLE 2 are plotted as a function of depth (down to at least 1 μm) are shown. The GDOES elemental depth profile provides the composition of the coating from the surface of the sample into the substrate, as well as the composition of the sample. (It should be understood that the GDOES analyses and methods of the present disclosure are not limited to aluminized coatings on 22MnB5 steel that are shown herein as examples.)

In FIG. 2A, the Aluminum content varies from about 66-68 wt. % Al at the surface of the coating and decreases to about 0.05 wt. % at a depth of about 24-25 μm. The Carbon content is fairly constant at below 0.25 wt. % C throughout the graph, because the wt. % Carbon is very low in the alloy and has low fidelity at this scale. The Manganese content is fairly constant at about 1 wt. % Mn throughout the graph, because the wt. % Manganese is also very low in the alloy and has low fidelity at this scale. The Silicon content varies from about 6-7 wt. % Si at the surface of the coating and decreases to about 0 wt. % at a depth of about 22-24 μm. Note the Silicon values in FIGS. 2A and 2B are measured values and not scaled (×10) values. Further, as explained in the SEM to GDOES comparisons below, the first Silicon values at the near surface include false readings and "noise" from impurities, while the second Silicon maximum is the coating side of the IDL. As further shown, the Iron content varies from about 0 wt. % at the surface of the coating and increases to about 96-98 wt. % at a depth of about 25-27 μm.

To illustrate the elements and how their intersections are being used in an innovative way, elemental analyses in the range of 22-28 μm are shown in greater detail in FIG. 2B. Here, the Aluminum content varies from 3 wt. % Al at a depth of about 23.25 μm from the surface of the coating and decreases to about 0.20-0.30 wt. % Al at a depth of about 25.6-25.8 μm. The Carbon content is now clearly increasing from about 0 wt. % C at a depth of about 22 μm to about 0.20-0.30 wt. % C at a depth of about 25.6-25.8 μm. As shown in FIG. 2B, the inventors found that Carbon, surprisingly, does not diffuse into the aluminized coating. Thus, enabling the Carbon to "delineate" the steel side of the IDL. The Manganese content varies from about 1 wt. % Mn at a depth of about 22 μm to about 1.1-1.2 wt. % Mn at a depth of about 25.6-25.8 μm. The Silicon content varies from about 1.3-1.4 wt. % at a depth of about 22 μm to about 0.20-0.30 wt. % C at a depth of about 25.6-25.8 μm. While the Iron is well above the 3 wt. % upper bound of FIG. 2B.

The inventors were surprised to discover that an improved IDL measurement is enabled by using the second Silicon maximum 66 (shown in this example at about 6-7 wt. % Si and about 16.8 μm deep) and the Aluminum and Carbon intersection 68 (shown in this example at about 0.20-0.30 wt. % and about 25.6-25.8 μm deep). More specifically, the intersection 68 between Aluminum and Carbon indicates the total thickness 14 of the aluminized coating, and a difference between the intersection 68 of Aluminum and Carbon and a second maximum 66 of Silicon wt. % indicates the thickness 18 of the IDL 16.

Validation and Verification of the GDOES QC Procedure

To validate and verify the unexpected results from the GDOES QC procedure of the present disclosure, the inventors compared the GDOES results with results from conventional SEM and OLM techniques. These validations are now described in greater detail.

Referring again to FIGS. 1A through 1D, and TABLE 1, OLM analyses of an aluminized 22MnB5 steel sample was performed that corresponds to different localized diameters of about 0.3 mm. As shown in TABLE 1, the average IDL thickness increases by at least 1 about 4.4 μm (about 4.83 μm in FIG. 1A to about 19.23 μm in FIG. 1D) from and the average coating thickness varies by at least about 29.6 μm (about 24.43 μm in FIG. 1A to about 54.03 μm in FIG. 1D) within the same part on a production line.

The variation in IDL thickness and coating thickness (averages and standard deviations) adversely affect material properties that include, but are not limited to: paintability, micro-cracking, surface ductility, surface hardness, and weldability. Therefore, these IDL thickness and coating thickness variances enable increased scrap, time, weight, and waste, and commiserate expense. Imprecise measurements that require a long time to acquire result in higher material thickness to provide adequate material properties. As material thicknesses increase the weight increases. Increases in weight result in increased maintainability.

Additionally, elemental depth profiles of the optically analyzed area are difficult and OLM analyses has the issues mentioned in the background. OLM elemental depth profiles are difficult because the operator must transfer the sample to another machine for elemental analysis and it is an exercise in futility to efficiently, regularly, and reliably find the same about 0.3 mm diameter area.

Figure 3A:
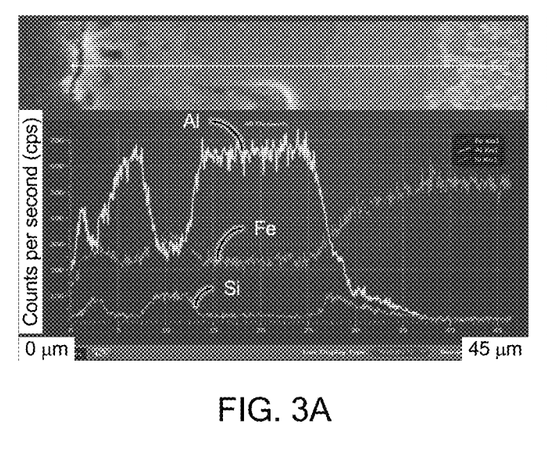
FIGS. 3A and 3B are graphs of exemplary scanning electron microscopy (SEM) and energy-dispersive X-ray spectroscopy (EDS) analysis of a sample of 22MnB5 steel, according to the investigations of the present disclosure.
Figure 3B:
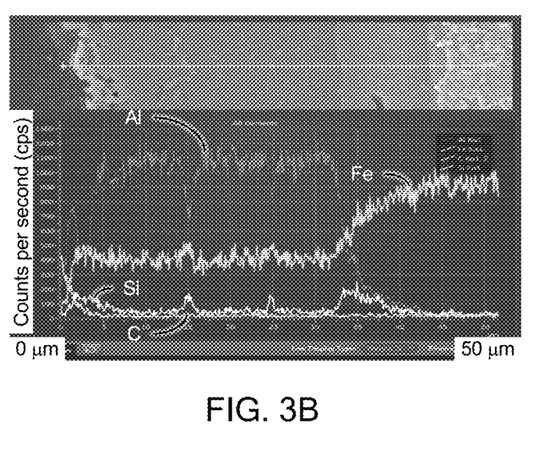

Now referring to FIGS. 3A and 3B, SEM analyses of an aluminized 22MnB5 steel sample were taken along 45 μm and 50 μm paths, which are about a tenth of the size of the OLM analyses in FIGS. 1A-1D. The SEM, through energy-dispersive X-ray spectroscopy (EDS), permits elemental depth profiles of the analyzed area. SEM analysis is more accurate than OLM, however, SEM sample preparation takes at least as much time as OLM sample preparation.

In FIG. 3A, Aluminum, Iron, and Silicon are graphed because, conventional IDL QC methods rely on Iron for measurement, while Aluminum and Silicon are used for coating related QC measurements. Here, the Aluminum has second minimum at a depth between about 9 μm and about 12 μm, which corresponds with the second Iron maximum, and would conventionally identify the thickness of the aluminized layer 14. Further, the Iron has an asymptote at a depth of about 36 μm, which is the commercial identification of the thickness 18 of the IDL 16, for a total IDL thickness of about 27 μm to about 24 μm. The Silicon has a second maximum at a depth between about 8.5 μm and about 12.5 μm and intersects Aluminum at a depth of about 35.75 μm.

In FIG. 3B, Aluminum, Carbon, Iron, and Silicon are graphed because of a discrepancy in the Aluminum—Iron overlap. Here, the Aluminum has a second minimum, at a depth between about 2 µm and about 3.5 µm, however, the Iron has a first maximum between about 1.5 µm and 4 µm. The Aluminum second minimum and the Iron second maximum were the expected overlap, but the 1 µm of variation in the overlaps is indicative that the iron and/or aluminum diffuse non-uniformly into the substrate and the coating. The carbon is fairly constant from about 5 µm, the values below 5 µm are believed to be "noise," but the Aluminum, Carbon, and Silicon converge between about 42.5 µm and about 45 µm. The Silicon has a second minimum between about 14.5 µm and 15.5 µm. It is noted, however, that FIG. 3A and FIG. 3B are from the same sample of aluminized 22MnB5 steel, indicative that the metallographic sample preparation for OLM and SEM-EDS analyses result in large variability with these inspection methods, and thus more samples must be analyzed, adding more overall time to the inspection methods.

Figure 4:
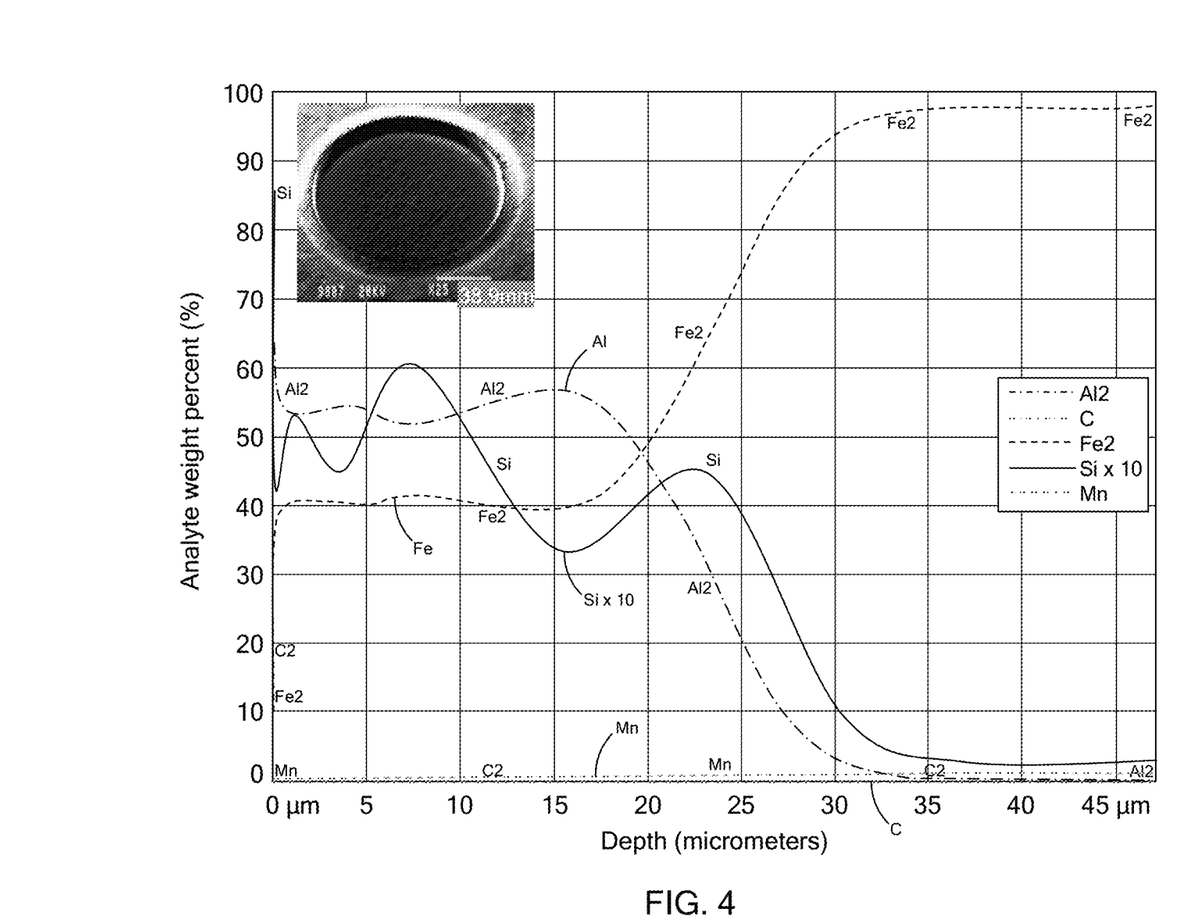
FIG. 4 is a graph of an exemplary GDOES analysis of the sample of FIG. 5A according to the teachings of the present disclosure.

Referring now to FIG. 4, the inventors analyzed the SEM sample of FIGS. 3A and 3B with a GDOES system and the methods according to the teachings of the present disclosure. The sample was tested in multiple (5 µm diameter) locations with nearly identical elemental curves, to verify the robustness of the GDOES results. Here, the second Aluminum minimum is shallow and has low-fidelity between about 6.5 µm and about 7.3 µm, and decreases to about 0 wt. % between about 34 µm and about 36 µm. The Carbon is fairly constant at below 1 wt. % C throughout the graph, because the wt. % Carbon is very low in the alloy and has low fidelity at this scale, similar to GDOES FIG. 2A and SEM FIG. 3B. The second Iron maximum is between about 6.5 µm and about 7.4 µm, however, the maximum is a broad low-fidelity peak, while the Iron asymptote is between about 32.5 and about 35 µm. The Silicon is a scaled (×10) measurement, with the second Silicon maximum between about 6.7 µm and about 6.9 µm, at a higher fidelity than the second Iron maximum, enabling a more accurate measurement of the thickness of the IDL.

The inventors analyzed higher fidelity GDOES results, similar to FIG. 2B, unexpectedly discovering that Carbon does not diffuse into the Aluminized coating. Because the Aluminum diffuses into the steel down to the concentration of Aluminum in the steel, while the Carbon does not diffuse into the aluminized coating, the intersection of the two elements (Aluminum and Carbon) is a higher fidelity steel side of the IDL, or in other words, the aluminized coating thickness 14. Thus, the GDOES method of the present disclosure calculates IDL thickness by measuring the distance between the second silicon maximum (coating side IDL boundary) and the intersection between the elemental profiles of Aluminum and Carbon (steel side IDL boundary).

The GDOES method according to the present disclosure calculates thicknesses by measuring the intersections between elemental profiles and different material combinations with different elemental profile intersections. For example, the GDOES method for aluminized boron steel calculates the coating thickness by measuring from the surface to the intersection between the Aluminum and Carbon elemental profiles. However, the GDOES for aluminized boron steel calculates the IDL thickness by measuring the difference between intersection of Aluminum and Carbon elemental profiles and second Silicon maximum elemental profile.

The GDOES QC is readily automated, which further reduces waste by increasing the number of measurements.

As shown in FIG. 4, the GDOES can analyze 5 mm diameter sections allowing for a more comprehensive analysis than SEM-EDS (1-2 µm sections), allowing for real-time (in situ) manufacturing line analysis. Moreover, as GDOES samples are less dependent (more invariant) on the skill of the person preparing the samples, the discrepancies in measurements are believed to be due to SEM sample preparation. Furthermore, GDOES results are more representative of the entire part than the locally measured OLM or SEM results.

As GDOES enables real-time QC measurements, the GDOES measurements allow reiterative tailoring of the manufacturing processes and controls (e.g. coating thickness, feed rate, furnace dew point, furnace ramp rates, furnace residence time, furnace temperature, furnace dwell time) to improve the desired material properties (e.g. paintability and weldability), to the specific sheet, coating, and manufacturing environment (e.g. humidity, dust, temperature). The reiterative real-time QC measurements coupled with manufacturing process and control adjustments reduce (improve) part size, weight, and cost. Ultimately, these improvements reduce the weight of the vehicle and thus enable improvements in fuel efficiency, maintainability, and a host of other lifecycle costs for the system.

Figure 5:
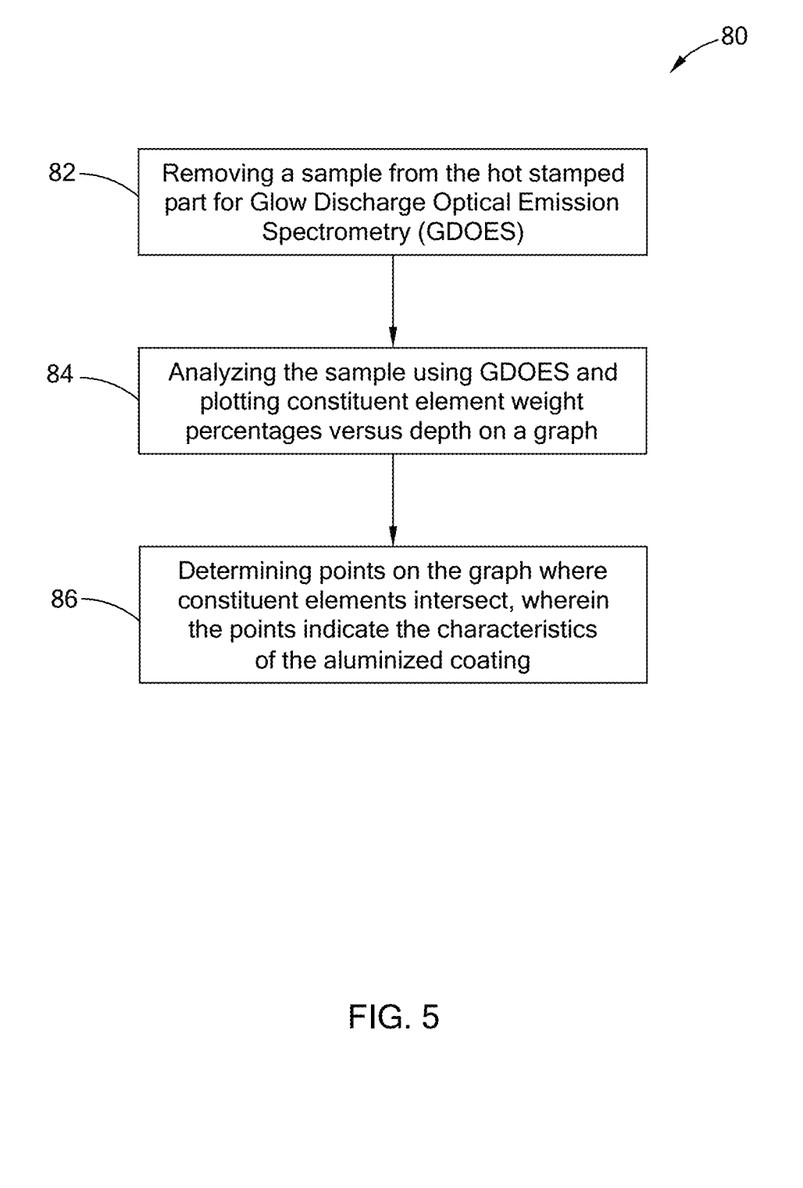
FIG. 5 is a flow diagram of an exemplary method of inspecting and determining characteristics of an aluminized coating of a hot stamped part according to the teachings of the present disclosure.

Referring to FIG. 5, in one form of the present disclosure, a method 80 of inspecting and determining characteristics of an aluminized coating of a hot stamped part is provided. At 82, the method 80 comprises removing a sample from the hot stamped part for GDOES. At 84, the method 80 comprises analyzing the sample using GDOES and plotting constituent element weight percentages versus depth on a graph. At 88, the method 80 comprises determining points on the graph where constituent elements intersect. In method 80 of the present disclosure, the points of intersection indicate the characteristics of the aluminized coating.

In another method of the present disclosure, the characteristics are selected from the group consisting of a total thickness of the aluminized coating, a thickness of an IDL, constituents of the aluminized coating, constituents of the hot stamped part, phase composition of the aluminized coating, surface oxidation, and weldability.

In various methods of the present disclosure, the hot stamped part is coated with a eutectic $AlSi_{10}Fe_3$ alloy, and an intersection between Aluminum and Carbon indicates the total thickness of the aluminized coating and the hot stamped part coated with a eutectic $AlSi_{10}Fe_3$ alloy, where a difference between an intersection of Aluminum and Carbon and a second maximum Silicon wt. % indicates the thickness of the IDL.

In at least one method of the present disclosure, the sample size is approximately 5 mm in diameter and the sample does not undergo any preparation prior to being analyzed by GDOES.

Alternately, in another method of the present disclosure, the sample may be prepared by mounting, grinding, and polishing.

While some methods of the present disclosure, further comprise determining whether contamination is present by a comparison of constituent elements to a known composition of the hot stamped part and the step of providing the characteristics to a subsequent manufacturing operation.

Figure 6:
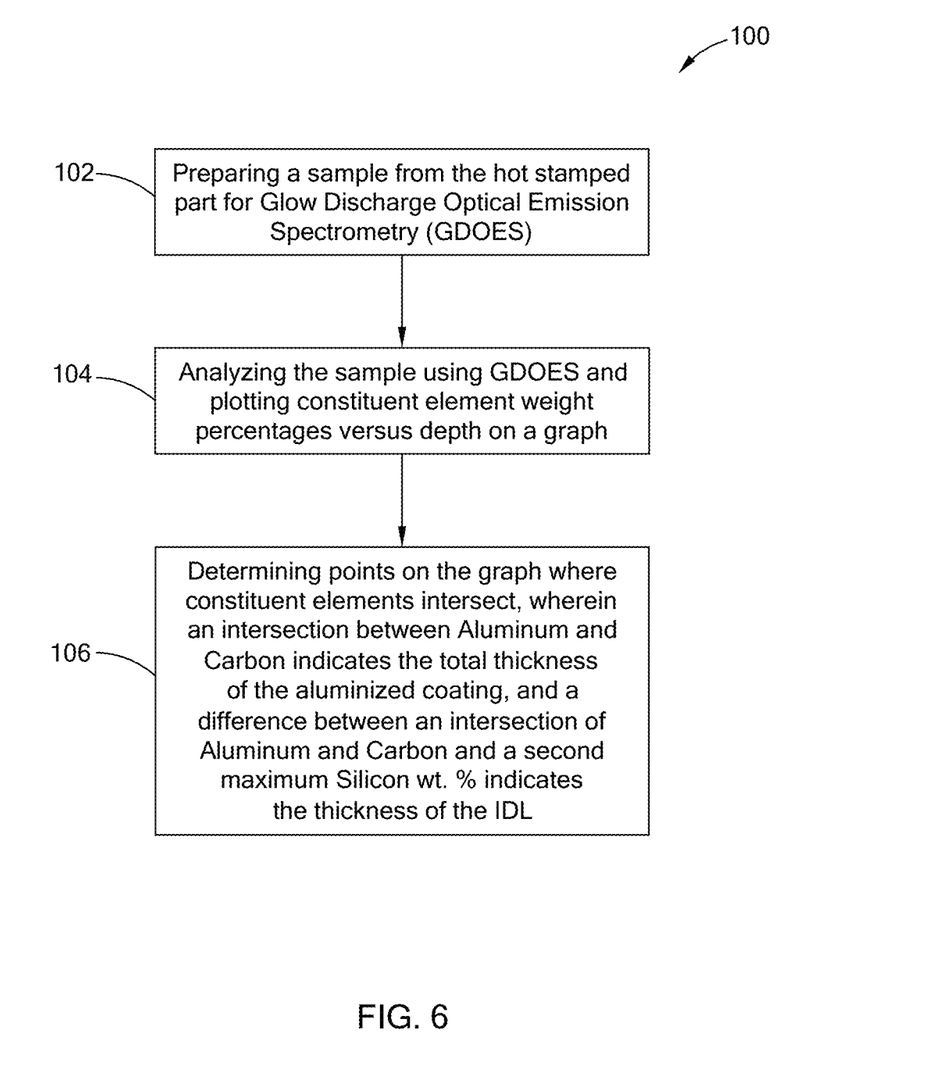
FIG. 6 is a flow diagram of an exemplary method of inspecting and determining a total thickness of an aluminized coating and a thickness of an IDL of a hot stamped boron steel part according to the teachings of the present disclosure.

Now referring to FIG. 6, in another form of the present disclosure, a method 100 of inspecting and determining a total thickness of an aluminized coating and a thickness of an IDL of a hot stamped boron steel part is provided. At step 102, the method 100 comprises preparing a sample from the hot stamped part for GDOES. At step 104, the method 100 comprises analyzing the sample using GDOES and plotting constituent element weight percentages versus depth on a graph. At step 106, the method 100 comprises determining points on the graph where constituent elements intersect. In method 100 of the present disclosure, the intersection between Aluminum and Carbon indicates the total thickness of the aluminized coating, and a difference between the intersection of Aluminum and Carbon and a second maximum Silicon wt. % indicates the thickness of the IDL.

A variation of the QC method of the present disclosure further comprises the step of providing the total thickness of the aluminized coating and the thickness of the IDL is provided to a controller of an annealing furnace. The controller of the annealing furnace can then use this information to adjust temperature and processing time. For example, if the coating thickness is lower than a specification, the annealing furnace may modify the processing time and/or temperature. Conversely, if the coating thickness is too high, the processing time and/or temperature can be modified. And because the QC method of the present disclosure can be carried out quickly, in less than about 15 minutes, process control feedback can be provided almost immediately to the annealing furnace in order to improve part yields.

Other methods of the present disclosure further comprise the step of providing the total thickness of the aluminized coating and the thickness of the IDL to a subsequent welding operation, wherein welding parameters are adjusted based on at least one of the total thickness of the aluminized coating and the thickness of the IDL.

Figure 7:
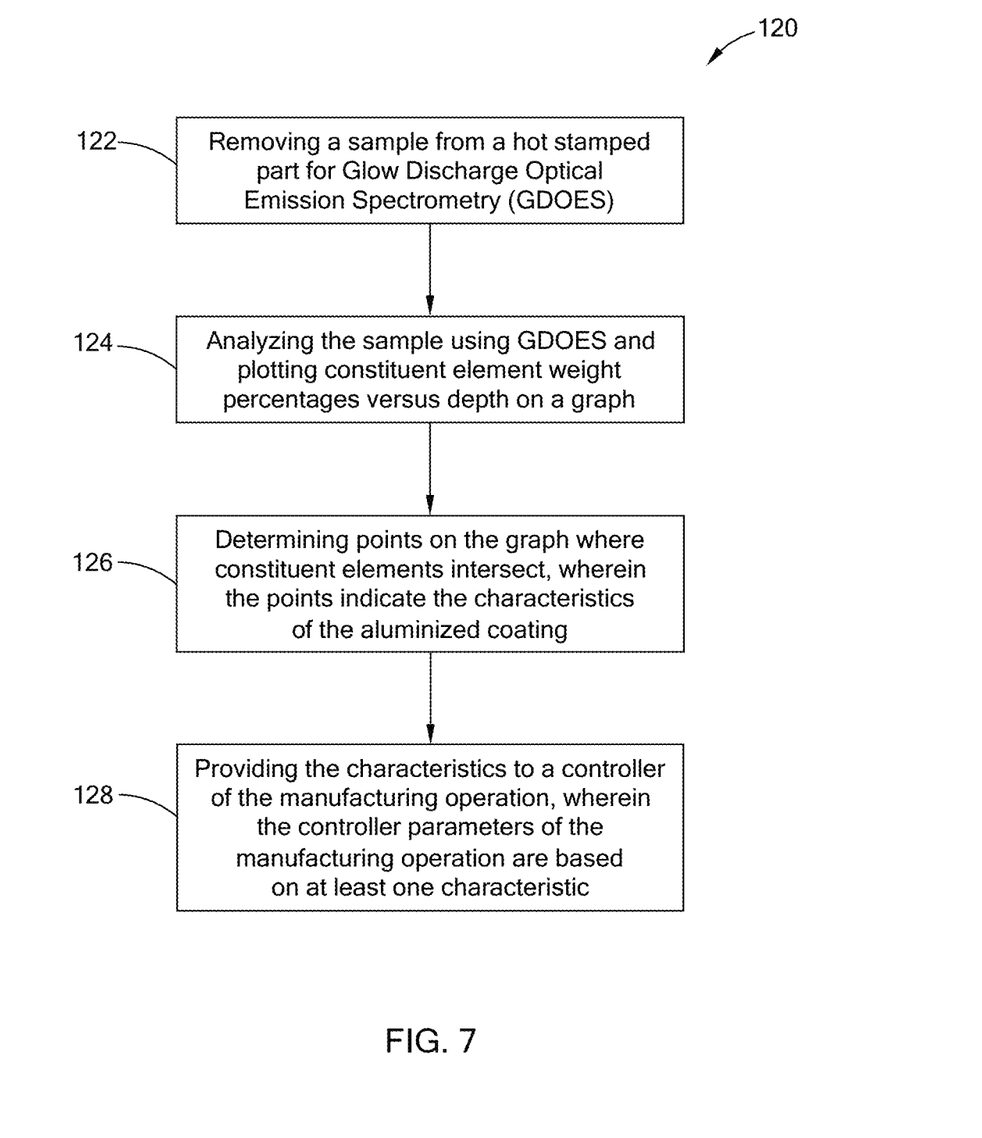
FIG. 7 is a flow diagram of an exemplary method of controlling a manufacturing operation for hot stamped parts according to the teachings of the present disclosure.

Referring to FIG. 7, a method 120 of controlling a manufacturing operation for hot stamped parts is provided according to the teachings of the present disclosure. At 122, the method 120 comprises removing a sample from a hot stamped part for GDOES. At 124, the method 120 comprises analyzing the sample using GDOES and plotting constituent element weight percentages versus depth on a graph. At 126, the method 120 comprises determining points on the graph where constituent elements intersect, wherein the points indicate the characteristics of the aluminized coating. At 128, the method 120 comprises providing the characteristics to a controller of the manufacturing operation, wherein the controller parameters of the manufacturing operation are based on at least one characteristic.

In at least one method of the present disclosure, the manufacturing operation or subsequent manufacturing operation is selected from the group consisting of an annealing operation, a shot-blasting operation, and a welding operation.

In yet another method of the present disclosure, the characteristics are provided to a controller of the annealing furnace, wherein the controller adjusts a temperature and processing time of the hot stamped part in the annealing furnace based on at least one characteristic.

These innovative QC methods of the present disclosure include sampling the hot stamped part and directly analyzing the samples without any sample preparation steps, such as:

No mounting the samples with an adhesive to create metallographic samples;
No grinding the metallographic samples;
No polishing the metallographic samples; and
No etching the metallographic samples.

The new GDOES QC methods and processes of the present disclosure provide many advantages over optical light microscopy (OLM) and industrial inspection, some of which include:

Reducing the time to measure IDL thickness from about 4 hours to about ≤15 minutes;
Reducing the time to measure total coating thickness from about 4 hours to about ≤15 minutes;
Reducing the time to measure IDL and total coating thicknesses from about 4 hours to about ≤15 minutes;
Improving the accuracy of thickness measurements (e.g. IDL and total) as compared to OLM techniques;
GDOES decreases metallographic laboratory costs as metallographic supplies, personnel, and time have reduced consumption;
GDOES output results are not operator dependent;
GDOES output results are not dependent upon sample preparation;
GDOES output results are highly applicable, can be integrated, comparable, operable, reliable, repeatable, robust, can be validated, and verifiable;
GDOES output results provide valuable information related to the coating characteristics;
GDOES output results are reciprocally related (can be correlated) to the temperature profile of the blank in the furnace;
GDOES output results are representative for the entire hot stamped part; and
GDOES output results correlate to weldability.

Further, GDOES output results provide valuable information related to the characteristics of the coatings. These GDOES output results are also reciprocally related (can be correlated) to the blank temperature profile in the furnace. Moreover, the GDOES output results are representative for the entire hot stamped part instead of the local areas of inspection from OLM methods. Unexpectedly, the GDOES output results correlate to weldability and enable improved welding efficiency.

Advantageously, GDOES enables adaptive annealing furnace controls based on GDOES output results. These adaptive annealing furnace controls promote efficiency, reduces scrap, and decreases production times.

As GDOES has nominal or negligible sample preparation, complete automation of this aspect of the QC process is achievable. Another improvement is that the enhanced accuracy, reliability, and repeatability of the GDOES processes enable customizable test reports that provide valuable information regarding chemical compositions (e.g. coating and of the steel substrate), phase compositions, thicknesses, oxidation, weldability, and many other manufacturing parameters. Further, GDOES can collect a wide range of data and tailoring the data for different desires.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method of inspecting and determining characteristics of an aluminized coating of a hot stamped part comprising:
removing a sample from the hot stamped part for Glow Discharge Optical Emission Spectrometry (GDOES);
analyzing the sample using GDOES and plotting constituent element weight percentages versus depth on a graph; and
determining points on the graph where constituent elements intersect,
wherein the points of intersection indicate the characteristics of the aluminized coating.

2. The method according to claim 1, wherein the characteristics are selected from the group consisting of a total thickness of the aluminized coating, a thickness of an inter-diffusion layer (IDL), constituents of the aluminized coating, constituents of the hot stamped part, phase composition of the aluminized coating, surface oxidation, and weldability.

3. The method according to claim 2, wherein the hot stamped part is coated with a eutectic $AlSi_{10}Fe_3$ alloy, and an intersection between Aluminum and Carbon indicates the total thickness of the aluminized coating.

4. The method according to claim 2, wherein the hot stamped part is coated with a eutectic $AlSi_{10}Fe_3$ alloy, and a difference between an intersection of Aluminum and Carbon and a second maximum Silicon wt. % indicates the thickness of the IDL.

5. The method according to claim 1, wherein the sample size is approximately 5 mm in diameter.

6. The method according to claim 1, wherein the sample does not undergo any preparation prior to being analyzed by GDOES.

7. The method according to claim 6, wherein the preparation includes mounting, grinding, and polishing.

8. The method according to claim 1 further comprising determining whether contamination is present by a comparison of constituent elements to a composition of the hot stamped part.

9. The method according to claim 1 further comprising the step of providing the characteristics to a subsequent manufacturing operation.

10. The method according to claim 9, wherein the subsequent manufacturing operation is selected from the group consisting of an annealing operation, a shot-blasting operation, and a welding operation.

11. The method according to claim 10, wherein the characteristics are provided to a controller of the annealing furnace, wherein the controller adjusts a temperature and processing time of the hot stamped part in the annealing furnace based on at least one characteristic.

12. A method of inspecting and determining a total thickness of an aluminized coating and a thickness of an inter-diffusion layer (IDL) of a hot stamped boron steel part comprising:
    preparing a sample from the hot stamped part for Glow Discharge Optical Emission Spectrometry (GDOES);
    analyzing the sample using GDOES and plotting constituent element weight percentages versus depth on a graph; and
    determining points on the graph where constituent elements intersect,
    wherein an intersection between Aluminum and Carbon indicates the total thickness of the aluminized coating, and a difference between an intersection of Aluminum and Carbon and a second maximum Silicon wt. % indicates the thickness of the IDL.

13. The method according to claim 12 further comprising determining whether contamination is present by a comparison of constituent elements to a composition of the hot stamped part.

14. The method according to claim 12 further comprising the step of providing the total thickness of the aluminized coating and the thickness of the IDL to a controller of an annealing furnace, wherein the controller adjusts a temperature and processing time of the hot stamped part in the annealing furnace based on at least one of the total thickness of the aluminized coating and the thickness of the IDL.

15. The method according to claim 12 further comprising the step of providing the total thickness of the aluminized coating and the thickness of the IDL to a subsequent welding operation, wherein welding parameters are adjusted based on at least one of the total thickness of the aluminized coating and the thickness of the IDL.

16. A method of controlling a manufacturing operation for hot stamped parts comprising:
    removing a sample from a hot stamped part for Glow Discharge Optical Emission Spectrometry (GDOES);
    analyzing the sample using GDOES and plotting constituent element weight percentages versus depth on a graph;
    determining points on the graph where constituent elements intersect,
    wherein the points indicate the characteristics of the aluminized coating; and
    providing the characteristics to a controller of the manufacturing operation, wherein the controller parameters of the manufacturing operation are based on at least one characteristic.

17. The method according to claim 16, wherein the characteristics are selected from the group consisting of a total thickness of the aluminized coating, a thickness of an inter-diffusion layer (IDL), constituents of the aluminized coating, constituents of the hot stamped part, phase composition of the aluminized coating, surface oxidation, and weldability.

18. The method according to claim 16, wherein the manufacturing operation is selected from the group consisting of an annealing operation, a shot-blasting operation, and a welding operation.

19. The method according to claim 16, wherein the hot stamped part is coated with a eutectic $AlSi_{10}Fe_3$ alloy, and an intersection between Aluminum and Carbon indicates the total thickness of the aluminized coating.

20. The method according to claim 16, wherein the hot stamped part is coated with a eutectic AlSi10Fe3 alloy, and a difference between an intersection of Aluminum and Carbon and a second maximum Silicon wt. % indicates the thickness of the IDL.

\* \* \* \* \*